United States Patent
Tsuji

(10) Patent No.: US 10,758,460 B2
(45) Date of Patent: Sep. 1, 2020

(54) GEL-LIKE COMPOSITION, AND EXTERNAL-USE AGENT FOR SKIN AND COSMETIC MATERIAL IN WHICH SAID GEL-LIKE COMPOSITION IS USED

(71) Applicant: KANEKA CORPORATION, Osaka (JP)

(72) Inventor: Tadao Tsuji, Osaka (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 16/353,410

(22) Filed: Mar. 14, 2019

(65) Prior Publication Data

US 2019/0209443 A1  Jul. 11, 2019

Related U.S. Application Data

(63) Continuation of application No. PCT/JP2017/033268, filed on Sep. 14, 2017.

(30) Foreign Application Priority Data

Sep. 14, 2016  (JP) .................. 2016-179634

(51) Int. Cl.

| | |
|---|---|
| A61K 8/04 | (2006.01) |
| A61K 8/34 | (2006.01) |
| A61K 8/64 | (2006.01) |
| B01J 13/00 | (2006.01) |
| A61K 8/31 | (2006.01) |
| A61Q 1/00 | (2006.01) |
| A61Q 5/00 | (2006.01) |
| A61Q 19/00 | (2006.01) |
| A61K 8/37 | (2006.01) |
| A61K 8/92 | (2006.01) |
| A61Q 19/10 | (2006.01) |

(52) U.S. Cl.
CPC ................ *A61K 8/042* (2013.01); *A61K 8/31* (2013.01); *A61K 8/34* (2013.01); *A61K 8/345* (2013.01); *A61K 8/37* (2013.01); *A61K 8/64* (2013.01); *A61K 8/92* (2013.01); *A61Q 1/00* (2013.01); *A61Q 5/00* (2013.01); *A61Q 19/00* (2013.01); *A61Q 19/10* (2013.01); *B01J 13/0065* (2013.01); *A61K 2800/5922* (2013.01)

(58) Field of Classification Search
CPC .................................. A61K 8/37; A61K 8/92
See application file for complete search history.

(56) References Cited

U.S. PATENT DOCUMENTS

| | | |
|---|---|---|
| 4,767,625 A | 8/1988 | Mitsuno et al. |
| 2004/0219125 A1 | 11/2004 | Yoneda et al. |
| 2011/0257116 A1 | 10/2011 | Kitagawa et al. |
| 2014/0178444 A1 | 6/2014 | Stadler et al. |

FOREIGN PATENT DOCUMENTS

| | | |
|---|---|---|
| JP | 2003012445 A | 1/2003 |
| JP | 2003113040 A | 4/2003 |
| JP | 2003176211 A | 6/2003 |
| JP | 2008069075 A | 3/2008 |
| JP | 200979030 A | 4/2009 |
| JP | 2012077044 A | 4/2012 |
| JP | 2012232963 A | 11/2012 |
| JP | 2014516997 A | 7/2014 |
| JP | 201627020 A | 2/2016 |
| WO | 9962482 A1 | 12/1999 |

OTHER PUBLICATIONS

International Search Report issued in International Application No. PCT/JP2017/033268; dated Oct. 24, 2017 (2 pages).
Written Opinion issued in International Application No. PCT/JP2017/033268; Dated Oct. 24, 2017 (5 pages).
Dr Straetmans Chemische Produkt GMBH: "Aminofect: a natural emulsifier (INCI: sodium surfactin)," Internet Citation, Nov. 5, 2005, XP002423075, Retrieved from the Internet: URL: http://web.archive.org/web/20051105021823/http://www-dr.straetmans.de/brochures/aminofect.pdf (2 pages).
Extended European Search Report issued in corresponding European Application No. 178509851; dated Aug. 13, 2019 (8 pages).
Office Action issued in corresponding Japanese Application No. 2018-539785; dated Sep. 3, 2019 (8 pages).
Office Action issued in corresponding Japanese Application No. 2018-539785, dated Feb. 4, 2020 (4 pages).

*Primary Examiner* — Kyle A Purdy
(74) *Attorney, Agent, or Firm* — Osha Liang LLP

(57) ABSTRACT

A gel-like composition includes a biosurfactant, a polyhydric alcohol, an oily component, and ethanol. The composition may have 0.01 to 10% by weight of the ethanol. The biosurfactant may be one or more selected from the group consisting of surfactin, arthrofactin, iturin, and a salt thereof.

6 Claims, No Drawings

GEL-LIKE COMPOSITION, AND EXTERNAL-USE AGENT FOR SKIN AND COSMETIC MATERIAL IN WHICH SAID GEL-LIKE COMPOSITION IS USED

TECHNICAL FIELD

One or more embodiments of the present invention relate to a gel-like composition characterized by containing a biosurfactant such as surfactin, and an external-use agent for skin and a cosmetic which use the gel-like composition.

BACKGROUND

Hitherto, various forms of cosmetics have been developed, and of them, a gel-like composition obtained by thickening an oily component (hereinafter, also referred to as "thickened gel-like oily composition") has been known and used for various external-use agents for skin and cosmetics such as cleansing cosmetics and cosmetics for hair. As the thickened gel-like oily composition, in the related art, a composition obtained by blending a polyhydric alcohol and a surfactant, and the like have been known, and for example, a gel-like composition containing surfactin, which is a biosurfactant, or an analogous compound thereof, or a salt thereof, and a trihydric or higher polyhydric alcohol has been known (Patent Document 1). Those gel-like compositions are absorbed quickly into the skin and exhibit a smooth feeling during use, but may have a low temporal stability caused by blending the polyhydric alcohol.
Patent Document 1: Japanese Unexamined Patent Application, Publication No. 2003-176211

SUMMARY

One or more embodiments of the present invention provide a gel-like composition that provides an external-use agent for skin and a cosmetic, which are absorbed quickly into the skin and exhibit a smooth feeling during use and excellent temporal stability, and an external-use agent for skin and a cosmetic which use the gel-like composition.

The present inventors have conducted intensive studies and have found that, by concurrently using a polyhydric alcohol and ethanol having a specific concentration in a gel-like composition containing a biosurfactant, the temporal stability of the gel-like composition is improved, and the gel-like composition having excellent feeling during use and excellent storage stability can be obtained, thereby completing one or more embodiments of the present invention. That is, one or more embodiments of the present invention relate to the following (1) to (7).

(1) A gel-like composition containing a biosurfactant, a polyhydric alcohol, an oily component, and ethanol, in which a content of the ethanol is 0.01% by weight to 10% by weight.

(2) The gel-like composition described in (1), in which the biosurfactant is one or more selected from the group consisting of surfactin, arthrofactin, iturin, and a salt thereof.

(3) The gel-like composition described in (1) or (2), in which the polyhydric alcohol is any one or two or more of trihydric or higher alcohols and polyether diols.

(4) The gel-like composition described in any one of (1) to (3), in which the polyhydric alcohol is any one or two or more of glycerin, sorbitol, xylitol, diglycerin, and polyethylene glycol.

(5) The gel-like composition described in any one of (1) to (4), in which a content of the polyhydric alcohol is 0.1% by weight to 30% by weight.

(6) An external-use agent for skin containing the gel-like composition described in any one of (1) to (5).

(7) A cosmetic containing the gel-like composition described in any one of (1) to (5).

According to one or more embodiments of the present invention, it is possible to provide a gel-like composition that provides an external-use agent for skin and a cosmetic, which are absorbed quickly into the skin and exhibit a smooth feeling during use and excellent temporal stability, and an external-use agent for skin and a cosmetic which use the gel-like composition.

DETAILED DESCRIPTION OF THE EMBODIMENTS

A gel-like composition of one or more embodiments of the present invention contains a biosurfactant. The biosurfactant is a natural compound which is produced by a microorganism, and has a very high stability to the environment and human body since the biosurfactant generally exhibits a high biodegradability and low skin irritation with respect to human body. Examples of the biosurfactant used in one or more embodiments of the present invention include a lipopeptide compound such as surfactin, arthrofactin, or iturin; a glycolipid biosurfactant such as mannosylerythritol lipid, sophorolipid, trehalose lipid, or rhamnolipid; a fatty acid biosurfactant such as spiculisporic acid; a polymer biosurfactant such as emulsan; and a salt thereof, but the biosurfactant is not limited thereto. The biosurfactant may be used solely, or two or more of the biosurfactants may be used.

Among the above examples, from the viewpoint that the stabilization effect of the gel-like composition with a small amount of the biosurfactant, in one or more embodiments a lipopeptide compound or a salt thereof is preferable, surfactin, arthrofactin, iturin, or a salt thereof is more preferable, and surfactin or a salt thereof is particularly preferable.

Herein, the salt of surfactin is a compound represented by General Formula (1):

[Chem. 1]

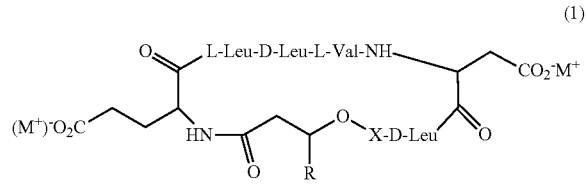

(1)

[in the formula, X represents an amino acid residue selected from the group consisting of a leucine residue, an isoleucine residue, and a valine residue; R represents a $C_{9-18}$ alkyl group; and $M^+$ represents an alkali metal ion or a quaternary ammonium ion].

In one or more embodiments, the amino acid residue as X may be either L form or D form, but is preferably L form.

The "$C_{9-18}$ alkyl group" indicates a linear or branched monovalent saturated hydrocarbon group with carbon atom number of 9 or more and 18 or less. Examples thereof include an n-nonyl group, a 6-methyloctyl group, a 7-methyloctyl group, an n-decyl group, a 8-methylnonyl group, an n-undecyl group, a 9-methyldecyl group, an n-dodecyl group, a 10-methylundecyl group, an n-tridecyl group, a 11-methyldodecyl group, an n-tetradecyl group, an n-pentadecyl group, an n-hexadecyl group, an n-heptadecyl group, and an n-octadecyl group.

The alkali metal ion of one or more embodiments is not particularly limited, but indicates a lithium ion, a sodium ion, a potassium ion, or the like.

Examples of a substituent of the quaternary ammonium ion include an organic group like an alkyl group such as a methyl group, an ethyl group, an n-propyl group, an isopropyl group, an n-butyl group, or a tert-butyl group; an aralkyl group such as a benzyl group, a methylbenzyl group, or a phenylethyl group; and an aryl group such as a phenyl group, a toluyl group, or a xylyl group. Examples of the quaternary ammonium ion include a tetramethyl ammonium ion, a tetraethyl ammonium ion, and a pyridinium ion.

In one or more embodiments, each of the surfactin and a salt thereof may be used solely, or two or more of the surfactins or the salts may be used.

In one or more embodiments, the surfactin or a salt thereof can be isolated from a culture broth prepared by culturing a microorganism such as a strain belonging to *Bacillus subtilis* in accordance with a known method. The surfactin or a salt thereof may be a purified product or an unpurified product. Further, for example, a culture broth can be directly used as the unpurified product. Further, the produce of the surfactin or a salt thereof obtained by a chemical synthesis method can be similarly used.

In the gel-like composition of one or more embodiments of the present invention, the concentration of the biosurfactant is preferably 0.01% by weight to 5% by weight, more preferably 0.05% by weight to 3% by weight, and further preferably 0.08% by weight to 2% by weight. In a case in which the concentration of the biosurfactant is 0.01% by weight or more, the surface-activating effect caused by the biosurfactant is easily obtained, and a stable gel-like composition is easily obtained. In a case in which the concentration of the biosurfactant is 5% by weight or less, a smooth feeling during use without stickiness is easily obtained.

The gel-like composition of one or more embodiments of the present invention contains a polyhydric alcohol. By containing the polyhydric alcohol, it is possible to obtain a gel-like composition which is absorbed quickly into the skin and exhibit a smooth feeling during use. Further, the polyhydric alcohol also has an effect of improving temporal stability of the gel-like composition by concurrently using ethanol, as described below.

Examples of the polyhydric alcohol include hydrocarbon diols such as alkane diols (for example, ethylene glycol, propylene glycol, butylene glycol, and the like); monoether diols such as diethylene glycol and dipropylene glycol; trihydric or higher alcohols such as glycerin, sorbitol, xylitol, and diglycerin; and polyether diols such as polyethylene glycol and polypropylene glycol. From the viewpoint of obtaining a more stable gel-like composition, any one or two or more of trihydric or higher alcohols and polyether diols may be preferably used, and any one or two or more of glycerin, sorbitol, xylitol, diglycerin, and polyethylene glycol may be particularly preferably used. Incidentally, in the present specification, the polyether diols refer to diols having a plurality of ether bonds. Therefore, the polyether diols also include triethylene glycol, tripropylene glycol, tetraethylene glycol, tetrapropylene glycol, and the like.

In the gel-like composition of one or more embodiments of the present invention, the concentration of the polyhydric alcohol is preferably 0.1% by weight to 30% by weight, more preferably 1% by weight to 30% by weight, and further preferably 3% by weight to 25% by weight. In a case in which the concentration of the polyhydric alcohol is 0.1% by weight or more, a stable gel-like composition is easily obtained. In a case in which the concentration of the polyhydric alcohol is 30% by weight or less, stickiness derived from the polyhydric alcohol hardly occurs and a smooth feeling during use is easily obtained.

The gel-like composition of one or more embodiments of the present invention contains an oily component. The oily component used in one or more embodiments of the present invention is not particularly limited as long as it is not mixed with water at any ratio, and preferred examples thereof include hydrocarbons such as squalane, fluid paraffin, light fluid isoparaffin, ceresin, polyethylene powder, squalene, microcrystalline wax, Vaseline, fluid isoparaffin, polybutene, or mineral oil; waxes such as bee wax, carnauba wax, candelilla wax, jojoba oil, lanolin, or whale wax; oils and fats such as macadamia oil, olive oil, cotton seed oil, soy bean oil, avocado oil, rice bran oil, rice oil, rice germ oil, palm seed oil, castor oil, rosehip oil, evening primrose oil, camellia oil, horse oil, grape seed oil, palm oil, meadow foam oil, shear butter, corn oil, safflower oil, or sesame oil; esters such as ethylhexyl palmitate, isononyl isononanoate, isopropyl myristate, ethyl oleate, glyceryl tri(caprylate-.capreate), cetyl 2-ethylhexanoate, glyceryl tri 2-ethylhexanoate, diisopropyl sebacate, or cholesteryl hydroxystearate; fatty acids such as myristic acid, stearic acid, or oleic acid; silicone oils such as methylpolysiloxane, methylphenylpolysiloxane, or amino-modified silicone; higher alcohols such as cetanol or oleyl alcohol; and alkyl glyceryl ethers such as batyl alcohol and chimyl alcohol. The oily component may be used solely, or two or more of the oily components may be used.

In the gel-like composition of one or more embodiments of the present invention, the concentration of the oily component is preferably 1% by weight to 99% by weight, more preferably 50% by weight to 99% by weight, and further preferably 60% by weight to 90% by weight. When the concentration of the oily component is within the above-described range, a stable thickened gel-like oily composition is easily obtained.

The gel-like composition of one or more embodiments of the present invention contains ethanol. By concurrently using the ethanol and polyhydric alcohol, the temporal stability of the gel-like composition is enhanced.

In the gel-like composition of one or more embodiments of the present invention, the concentration of the ethanol is 0.01% by weight to 10% by weight, preferably 0.5% by weight to 9% by weight, and more preferably 0.1% by weight to 8% by weight. In a case in which the concentration of the ethanol is less than 0.01% by weight or more than 10% by weight, the temporal stability of the gel-like composition may be insufficient.

In the gel-like composition of one or more embodiments of the present invention, arbitrary components can be blended in the range that the effect of one or more embodiments of the present invention is achieved. Examples of the arbitrary components include water, nonionic surfactants, anionic surfactants, cationic surfactants, ampholytic surfactants, thickeners, ultraviolet absorbers, antioxidants, emollient agents, emulsifiers, solubilizers, anti-inflammatory agents, moisturizing agents, preservatives, fungicides, pH adjusters, dyes, perfumes, and powders.

The gel-like composition of one or more embodiments of the present invention can be prepared, for example, by dissolving a biosurfactant in a polyhydric alcohol to obtain a solution and adding an oily component little by little to the solution under stirring, or the like.

In one or more embodiments, the oily component may be added in a predetermined amount little by little (split addition) or may be continuously added (continuous addition).

In the case of split addition, the oily component may be added at a time, for example, in an amount of 60% by mass or less, preferably 30% by mass or less, and more preferably 10% by mass or less of the amount of the polyhydric alcohol which has been already added, and is stirred and uniformed. By repeating this operation, a necessary amount of the oily component is added.

In the case of continuous addition, the addition speed of the oily component may be, for example, 60% by mass/min or less, preferably 30% by mass/min or less, and more preferably 10% by mass/min or less of the amount of the polyhydric alcohol which has been already added.

Further, in the case of adding other components, any method of adding other components before adding the oily component, dissolving or dispersing other components in the oily component and then adding the other components, adding other components after adding the whole amount of the oily component, or adding other components in the middle of adding the oily component may be employed. The whole amount of the polyhydric alcohol may be added first, or some of addition amount thereof may be used first and then the remaining amount may be added thereafter.

Preferred examples of use application of the gel-like composition of one or more embodiments of the present invention include an external-use agent for skin and a cosmetic, and for example, the gel-like composition can be used suitably for basic cosmetics such as cream, lotion, cleansing gel, and cleansing cream; make-up cosmetics such as foundation, eye shadow, lip color, and lip gloss; cosmetics for hair such as hair cream, styling gel, and hair wax; and cleansing materials such as shampoo, hair conditioner, hand soap, body soap, and cleansing foam.

EXAMPLES

The gel-like composition of one or more embodiments of the present invention is prepared, for example, in the following manner, but the present invention is not limited thereto.

Example 1

(A) Sodium surfactin 0.3% by weight
(B) Glycerin 9% by weight
(C) Ethanol 1% by weight
(D) Squalane 86.4% by weight
(E) Purified water 3% by weight
(F) Phenoxyethanol 0.3% by weight (A) and (C) were put in (B) and dissolved under stirring. Thereafter, (D) was gradually put therein to obtain a gel-like composition. (F) and (E) were gradually put therein under stirring to prepare a gel-like composition having the composition presented in Table 1. Incidentally, the unit of numerical values in Table 1 is % by weight.

Example 2

A gel-like composition was prepared in the same method as in Example 1, except that the amount of the component (B) was changed to 7% by weight and the amount of the component (C) was changed to 3% by weight.

Comparative Example 1

A gel-like composition was prepared in the same method as in Example 1, except that the amount of the component (B) was changed to 10% by weight and the component (C) was not used.

Comparative Example 2

A gel-like composition was prepared in the same method as in Example 1, except that propanol was used as the component (C).

Comparative Example 3

A gel-like composition was prepared in the same method as in Example 1, except that butanol was used as the component (C).

Comparative Example 4

A gel-like composition was prepared in the same method as in Example 1, except that 1,3-butylene glycol was used as the component (C).

Comparative Example 5

A gel-like composition was prepared in the same method as in Example 2, except that propanol was used as the component (C).

Comparative Example 6

A gel-like composition was prepared in the same method as in Example 2, except that butanol was used as the component (C).

Comparative Example 7

A gel-like composition was prepared in the same method as in Example 2, except that 1,3-butylene glycol was used as the component (C).

Comparative Example 8

A gel-like composition was prepared in the same method as in Example 1, except that the component (B) was not used and the amount of the component (D) was changed to 95.4% by weight.

Example 3

(A) Sodium surfactin 1% by weight
(B) Glycerin 19.9% by weight
(C) Ethanol 0.1% by weight
(D) Squalane 76% by weight
(E) Purified water 3% by weight (A) and (C) were put in (B) and dissolved under stirring. Thereafter, (D) was gradually put therein to obtain a gel-like composition. (E) was gradually put therein under stirring to prepare a gel-like composition having the composition presented in Table 2. Incidentally, the unit of numerical values in Table 2 is % by weight.

Example 4

A gel-like composition was prepared in the same method as in Example 3, except that the amount of the component (B) was changed to 19.5% by weight and the amount of the component (C) was changed to 0.5% by weight.

Example 5

A gel-like composition was prepared in the same method as in Example 3, except that the amount of the component (B) was changed to 19% by weight and the amount of the component (C) was changed to 1% by weight.

Example 6

A gel-like composition was prepared in the same method as in Example 3, except that the amount of the component (B) was changed to 17% by weight and the amount of the component (C) was changed to 3% by weight.

Example 7

A gel-like composition was prepared in the same method as in Example 3, except that the amount of the component (B) was changed to 15% by weight and the amount of the component (C) was changed to 5% by weight.

Example 8

A gel-like composition was prepared in the same method as in Example 3, except that the amount of the component (B) was changed to 20% by weight, the amount of the component (C) was changed to 3% by weight, and the amount of the component (D) was changed to 73% by weight.

Example 9

A gel-like composition was prepared in the same method as in Example 3, except that the amount of the component (B) was changed to 20% by weight, the amount of the component (C) was changed to 8% by weight, and the amount of the component (D) was changed to 68% by weight.

Comparative Example 9

A gel-like composition was prepared in the same method as in Example 3, except that the amount of the component (B) was changed to 20% by weight and the component (C) was not used.

Comparative Example 10

A gel-like composition was prepared in the same method as in Example 5, except that propanol was used as the component (C).

Comparative Example 11

A gel-like composition was prepared in the same method as in Example 5, except that butanol was used as the component (C).

Comparative Example 12

A gel-like composition was prepared in the same method as in Example 5, except that 1,3-butylene glycol was used as the component (C).

<Stability Evaluation>

Regarding Examples 1 and 2 and Comparative Examples 1 to 8, the appearance of the gel-like composition was evaluated after the gel-like composition having the composition presented in Table 1 was left to stand still at 50° C. for 4 weeks. Regarding Examples 3 to 9 and Comparative Example 9 to 12, the appearance of the gel-like composition was evaluated after the gel-like composition having the composition presented in Table 2 was left to stand still at 50° C. for 12 weeks. The results are presented in Table 1 and Table 2. In Examples 1 to 9, no syneresis of oil was observed or only very little seepage of oil was observed, and the storage stability of the gel-like composition was excellent; on the other hand, in Comparative Examples 1 to 12, syneresis of oil was observed and affected the storage stability of the gel-like composition. As described above, it was found that, by concurrently using a polyhydric alcohol and ethanol having a predetermined concentration, the temporal stability of the gel-like composition is improved.

TABLE 1

|  | Example 1 | Example 2 | Comparative Example 1 | Comparative Example 2 | Comparative Example 3 | Comparative Example 4 |
|---|---|---|---|---|---|---|
| SF | 0.3 | 0.3 | 6.3 | 6.3 | 6.3 | 0.3 |
| Glycerin | 9 | 7 | 10 | 9 | 9 | 9 |
| Ethanol | 1 | 3 |  |  |  |  |
| Propanol |  |  |  | 1 |  |  |
| Butanol |  |  |  |  | 1 |  |
| 1,3Butylene glycol |  |  |  |  |  | 1 |
| Squalane | 86.4 | 86.4 | 86.4 | 86.4 | 86.4 | 86.4 |
| Phenoxyethanol | 0.3 | 0.3 | 0.3 | 0.3 | 0.3 | 0.3 |
| Purified water | 3 | 3 | 3 | 3 | 3 | 3 |
| Total | 100 | 100 | 100 | 100 | 100 | 100 |
| Stability evaluation result (50° C. 4 W) | ○ | Δ | X | X | X | X |

|  | Comparative Example 6 | Comparative Example 6 | Comparative Example 7 | Comparative Example 8 |
|---|---|---|---|---|
| SF | 0.3 | 0.3 | 0.3 | 0.3 |
| Glycerin | 7 | 7 | 7 | 0 |
| Ethanol |  |  |  | 1 |
| Propanol | 3 |  |  |  |
| Butanol |  |  | 3 |  |
| 1,3Butylene glycol |  | 3 |  | 3 |

TABLE 1-continued

| | | | | |
|---|---|---|---|---|
| Squalane | 86.4 | 86.4 | 86.4 | 95.4 |
| Phenoxyethanol | 0.3 | 0.3 | 0.3 | 0.3 |
| Purified water | 3 | 3 | 3 | 3 |
| Total | 100 | 100 | 100 | 100 |
| Stability evaluation result (50° C. 4 W) | X | X | X | X |

TABLE 2

| | Example 3 | Example 4 | Example 5 | Example 6 | Example 7 | Example 8 |
|---|---|---|---|---|---|---|
| SF | 1 | 1 | 1 | 1 | 1 | 1 |
| Glycerin | 19.9 | 19.5 | 19 | 17 | 15 | 20 |
| Ethanol | 0.1 | 0.5 | 1 | 3 | 5 | 3 |
| Propanol | | | | | | |
| Butanol | | | | | | |
| 1,3Butylene glycol | | | | | | |
| Squalane | 76 | 76 | 76 | 76 | 76 | 73 |
| Phenoxyethanol | | | | | | |
| Purified water | 3 | 3 | 3 | 3 | 3 | 3 |
| Total | 100 | 100 | 100 | 100 | 100 | 100 |
| Stability evaluation result (50° C. 12 W) | Δ | ○ | ○ | ○ | ○ | ○ |

| | Example 9 | Comparative Example 9 | Comparative Example 10 | Comparative Example 11 | Comparative Example 12 |
|---|---|---|---|---|---|
| SF | 1 | 1 | 1 | 1 | 1 |
| Glycerin | 20 | 20 | 19 | 19 | 19 |
| Ethanol | | 8 | | | |
| Propanol | | | 1 | | |
| Butanol | | | | 1 | |
| 1,3Butylene glycol | | | | | 1 |
| Squalane | 68 | 76 | 76 | 76 | 76 |
| Phenoxyethanol | | | | | |
| Purified water | 3 | 3 | 3 | 3 | 3 |
| Total | 100 | 100 | 100 | 100 | 100 |
| Stability evaluation result (50° C. 12 W) | Δ | X | X | X | X |

<Stability Evaluation Criteria>
○ (good): no separated (no syneresis of oil)
Δ (slightly good): slightly separated (very little seepage of oil)
X (poor): separated (syneresis of oil)

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:
1. A gel-like composition, comprising:
    a biosurfactant;
    a polyhydric alcohol;
    an oily component; and
    ethanol,
    wherein the composition comprises 0.1 to 8% by weight of the ethanol 60 to 90% by weight of the oily component, and 0.1 to 30% by weight of the polyhydric alcohol, and
    wherein the polyhydric alcohol is one or more selected from the group consisting of trihydric or higher alcohols and polyether diols.
2. The gel-like composition according to claim 1, wherein the biosurfactant is one or more selected from the group consisting of surfactin, arthrofactin, iturin, and a salt thereof.
3. The gel-like composition according to claim 1, wherein the polyhydric alcohol is one or more selected from the group consisting of glycerin, sorbitol, xylitol, diglycerin, and polyethylene glycol.
4. An external-use agent for skin, comprising the gel-like composition according to claim 1.
5. A cosmetic, comprising the gel-like composition according to claim 1.
6. A gel-like composition, comprising:
    0.01 to 5% by weight of a biosurfactant;
    0.1 to 30% by weight of a polyhydric alcohol;
    60 to 90% by weight of an oily component; and
    0.1 to 8% by weight of ethanol,
    wherein the polyhydric alcohol is one or more selected from the group consisting of glycerin, sorbitol, xylitol, diglycerin, and polyethylene glycol.

* * * * *

UNITED STATES PATENT AND TRADEMARK OFFICE
CERTIFICATE OF CORRECTION

PATENT NO. : 10,758,460 B2
APPLICATION NO. : 16/353410
DATED : September 1, 2020
INVENTOR(S) : Tadao Tsuji It is certified that error appears in the above-identified patent and that said Letters Patent is hereby corrected as shown below:

In the Claims

At Column 9, Claim number 1, Line number 62, the portion "the ethanol 60 to 90%" should read -- the ethanol, 60 to 90% --.

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*